United States Patent [19]

Megerle

[11] Patent Number: 5,089,780
[45] Date of Patent: Feb. 18, 1992

[54] OIL QUALITY MONITOR SENSOR AND SYSTEM

[75] Inventor: Clifford A. Megerle, Thousand Oaks, Calif.

[73] Assignee: Hughes Aircraft Company, Los Angeles, Calif.

[21] Appl. No.: 663,770

[22] Filed: Mar. 4, 1991

Related U.S. Application Data

[63] Continuation of Ser. No. 417,118, Oct. 4, 1989, abandoned.

[51] Int. Cl.⁵ .......................................... G01N 27/413
[52] U.S. Cl. ................................. 324/448; 324/444; 324/694; 324/698
[58] Field of Search ............... 324/438, 439, 450, 444, 324/446, 448, 442, 698, 693, 713, 71.1, 694; 73/64, 116

[56] References Cited

U.S. PATENT DOCUMENTS

| | | | |
|---|---|---|---|
| 3,502,970 | 3/1970 | Thayer | 73/64 |
| 4,417,212 | 11/1983 | Baum | 324/439 |
| 4,646,070 | 2/1987 | Yasuhara et al. | 73/64 X |
| 4,701,713 | 10/1987 | Eaton et al. | 324/439 X |
| 4,741,204 | 5/1988 | Luck et al. | 73/64 X |
| 4,791,374 | 12/1988 | Yodice et al. | 324/439 |
| 4,808,931 | 2/1989 | Ling | 324/439 X |

*Primary Examiner*—Kenneth A. Wieder
*Attorney, Agent, or Firm*—M. E. Lachman; W. J. Streeter; W. K. Denson-Low

[57] ABSTRACT

A sensor and system for monitoring the accumulation of contaminants in oil wherein the contaminants have an electrical conductivity which is different from the oil. An electrochemical cell is used to measure the alternating current conductivity of the oil to provide an indication of the amount of contaminants present in the oil. Acids and water are two common engine oil contaminants which are accurately monitored by this alternating current conductivity measurement system.

10 Claims, 1 Drawing Sheet

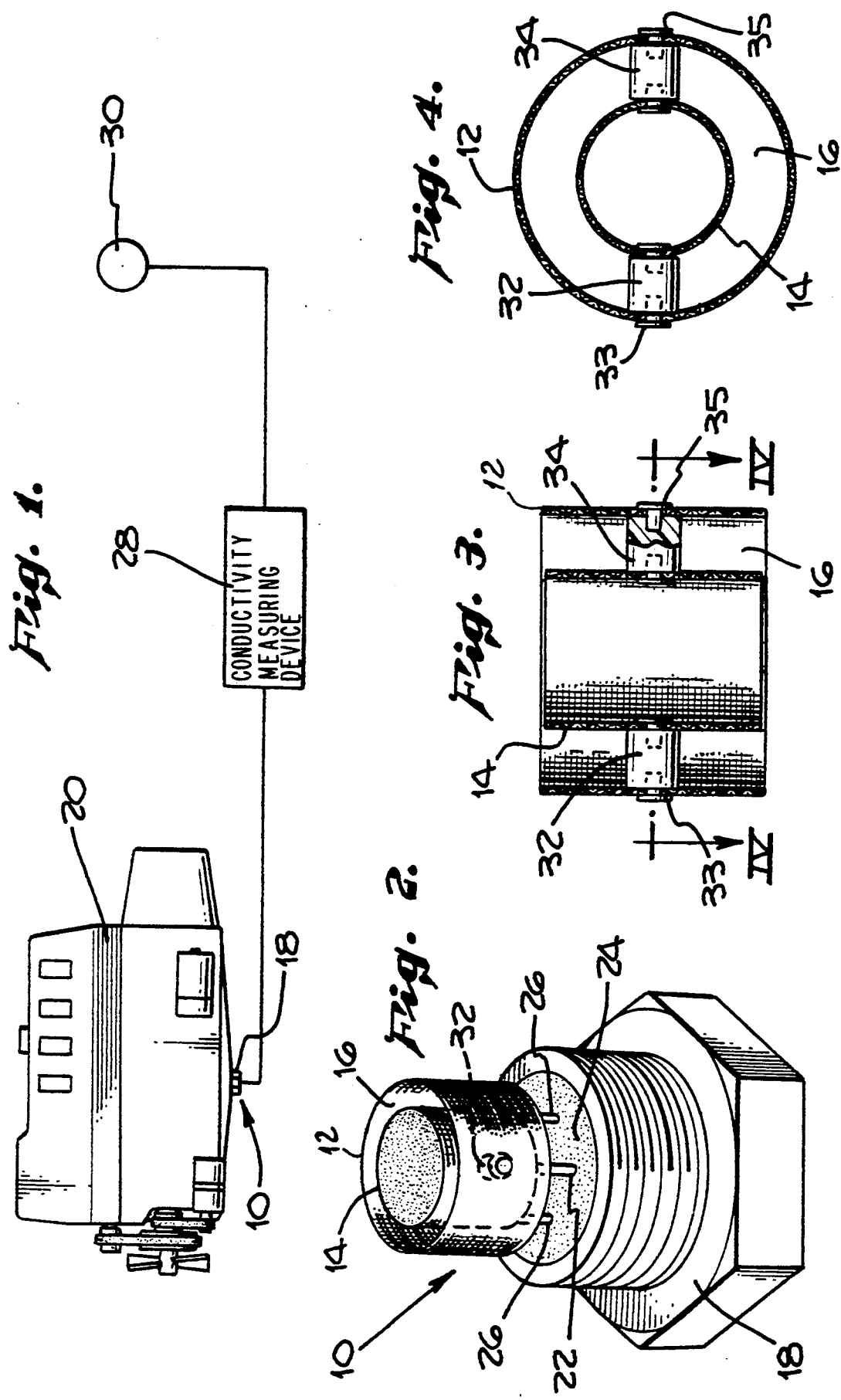

OIL QUALITY MONITOR SENSOR AND SYSTEM

This is a continuation of application Ser. No. 07/417,118, filed Oct. 4, 1989 now abandoned.

BACKGROUND OF THE INVENTION

1. Field of the Invention

The present invention relates generally to determining the degree of contamination of oil. More particularly, the present invention relates to a monitor sensor and system for monitoring the accumulation of contaminants in engine oil.

2. Description of Related Art

Oxidation products, such as water and sulfuric acid, accumulate in motor oil during operation of the engine. The build-up of these contaminants can corrode the internal surfaces of the engine. Since these contaminants are not removed by conventional filtration methods, the oil must be changed when the levels of these species increase beyond acceptable limits. Prolonged operation of an engine having high levels of contaminants in the oil can lead to premature engine failure or other corrosion related problems.

Currently, the lifetime of engine oil is usually determined according to mileage or time limits wherein the oil is automatically replaced after established limits are reached. Such mileage or time limits are based on operation of the engine under normal operating conditions and operation within normal limits. The problem with such established oil change schedules is that contaminants may build up at a higher or lower rate depending upon the operating environment of the engine. As a result, the engine may be subjected to unduly high contaminant levels or on the other hand, oil may be wasted due to unneeded replacement when contaminant concentrations are still below acceptable levels.

It would be desirable to provide a system for continually monitoring the contaminant concentrations in engine oil to provide a constant measure of engine oil quality. Such a system would provide the operator with an accurate measurement of oil quality and an indication of whether or not the oil should be changed. Such a system will remove the uncertainties with regards to contaminant levels that are inherent in the presently used mileage- or time- based oil change schedules.

SUMMARY OF THE INVENTION

In accordance with the present invention, a sensor and system are provided for monitoring the accumulation of contaminants in engine oil wherein the contaminants have an electrical conductivity which is different from the oil.

The present invention is based on the discovery that measurement of the alternating current conductivity of oil provides an accurate indication of contaminant levels in the oil. Contaminants, such as sulfuric acid and water have alternating current conductivities which are substantially higher than those of oil. Accordingly, the accumulation of such contaminants can be measured accurately. Further, the use of alternating current measurements is particularly well-suited for the noisy electrical environment present in internal combustion engines.

As a feature of the present invention, the monitoring system includes an electrochemical cell having two concentric electrodes which are spaced apart a sufficient distance to provide a conductivity measurement zone located between the electrodes. The system further includes an alternating current conductivity measurement system which measures the alternating current conductivity of oil located between the two concentric electrodes. The measurement device is set up to provide continual read-out of contaminant levels or it can be designed to actuate a warning light when unacceptable levels of alternating current conductivity are reached.

The alternating current conductivity sensor and system in accordance with the present invention provide an accurate and continuous indication of contaminant levels in the engine oil which eliminates the problems inherent in changing oil on a fixed mileage or time schedule. In addition, the simplicity and durability of the electrode sensor is well-suited for use in the relatively harsh conditions present in the interior of an internal combustion engine.

The above-discussed and many other features and attendant advantages of the present invention will become apparent as the invention becomes better understood by reference to the following detailed description when considered in conjunction with the accompanying drawings.

BRIEF DESCRIPTION OF THE DRAWINGS

FIG. 1 is a partially schematic representation of a preferred exemplary system in accordance with the present invention for monitoring the accumulation of contaminants in an internal combustion engine.

FIG. 2 is a perspective view of a preferred exemplary sensor in accordance with the present invention.

FIG. 3 is a side sectional view of exemplary preferred concentric electrodes in accordance with the present invention.

FIG. 4 is a sectional view of FIG. 3 taken in the IV—IV plane.

DESCRIPTION OF PREFERRED EMBODIMENTS

The sensor and system of the present invention may be used to monitor the quality of oil in a wide variety of circumstances. However, the sensor and system are especially well-suited for monitoring oil quality in internal combustion engines where oxidation products such as water and sulfuric acid form in the oil. The following description will be limited to the monitoring of oil in such internal combustion engines with it being understood that the invention may be used to monitor oil quality in other situations.

In accordance with the present invention, alternating current (AC) conductivity is used to determine the levels of contaminants in the oil which have an electrical conductivity different from the oil. Sulfuric acid and water are two contaminants which have conductivities which are substantially different from oil. The conductivity of sulfuric acid is on the order of $1 \times 10^{-2}$ (Ohm-cm)$^{-1}$ while the conductivity of pure water is on the order of $8 \times 10^{-7}$ (Ohm-cm)$^{-1}$. The conductivity of water containing ionic species, as are present in an engine crankcase, is higher than $8 \times 10^{-7}$ (Ohm-cm)$^{-1}$. This is to be contrasted with oil which has a conductivity on the order of less than $1 \times 10^{-8}$ (Ohm-cm)$^{-1}$.

In accordance with the present invention a small electrochemical cell is placed in the oil and an AC voltage is impressed across the electrodes. The current that passes through the cell is a measure of the conductivity of the oil. AC voltage, rather than DC voltage is used for two reasons. First, the use of AC voltage is less subject to concentration polarization effects and is also less subject to electrode contamination through the electrochemical formation of corrosion products or adherent contaminant species at the electrode surfaces. Secondly, small alternating currents are more easily measured, in electrically noisy environments, than are small direct currents.

The considerations which are taken into account in designing the electrodes are as follows. The resistance of a liquid occupying the area between parallel plate electrodes is given by the following equation:

$$R = r(L/A) \quad (1)$$

where R is the resistance in Ohms, r is the resistivity of the liquid in the Ohm-cm, L is the spacing between the electrodes in cm and A is the area of the electrodes in $cm^2$. The conductivity of the oil, k, is the reciprocal of its resistivity:

$$K = 1/r = (1/R)(L/A) \quad (2)$$

and has units of $(Ohm-cm)^{-1}$.

In general, it is difficult to make accurate measurements of L and A for an as-fabricated electrochemical cell. However, it is relatively easy to measure the value of L/A by preparing a standard solution of known conductivity and measuring the resistance of the cell. Preferably, potassium chloride solutions of varying normalities are used for this purpose. In practice the value of L/A is measured experimentally and is used as a cell constant for all future measurements. In the present instance, K is the cell constant having a value of $$K = L/A = k' R' \quad (3)$$

where k' is the conductivity of the standard solution and R' is the resistance of the standard solution in the cell. The conductivity of an unknown solution then becomes, by equation (2), $$k = K(1/R) \quad (4)$$

A preferred exemplary sensor in accordance with the present invention is shown generally at 10 in FIGS. 1 and 2. The conductivity cell includes concentric cylindrical electrodes 12 and 14. The electrodes may be made from a variety of materials including stainless steel or gold-plated stainless steel. The concentric cylinders 12 and 14 can be in the form of solid sheets, perforated sheets or wire mesh. The openings in the perforated sheets or wire mesh should be on the order of 0.1 millimeters (mm) to 10.0 mm. Perforated sheets or wire mesh are preferred since they provide constant flow through the electrodes 12 and 14 to provide uniform mixing of oil in the cylindrical zone 16 located between the electrodes 12 and 14.

The electrodes 12 and 14 are mounted on a plug or other structure so that they can be immersed in the engine oil. The plug 18 is designed to be mounted in the oil sump, or otherwise in the oil stream, of the internal combustion engine 20 as best shown in FIG. 1. The outer electrode 12 includes mounting pins 22 (only one shown) which are embedded in an insulating material 24. The insulating material 24 may be a ceramic or other conventional potting material used for mounting electronic devices. The inner electrode 14 is mounted within the insulating material by pins 26. The outer mounting pins 22 are grounded by connection to the drain plug 18. Other means for grounding the outer electrode 12 may be used if desired.

The inner electrode 14 is connected by way of pins 26 to an AC conductivity measuring device 28 (see FIG. 1). The pins 26 are preferably connected to a single electrical feed-through which penetrates the insulating material and does not come in contact with the metal portion of the drain plug 18.

The conductivity measuring device 28 is connected to a warning light 30 or other display device which provides the operator of engine 20 with an indication of the oil conductivity. The indicator 30 may be a digital or analog device which gives a continual oil quality reading. Alternatively, the indicator 30 may be a warning light which is activated only when the conductivity measuring device 28 registers conductivities above a predetermined level, such as approximately $1 \times 10$ $(Ohm-cm)^{-1}$, for example.

The conductivity measuring device 28 preferably is an electronics module which will allow stand-alone operation of the sensor and will have an output that provides continual input to an oil quality gauge or power to a warning light or LED when the maximum acceptable oil conductivity level has been exceeded. The conductivity measuring device 28 will supply alternating current voltage to the sensor electrodes 12 and 14 at a frequency that differs as much as possible from the highest intensity noise frequencies within the automobile. Alternating current frequencies within the range of 100 Hz to 1000 Hz are preferred, but higher and lower frequencies can also be used. Preferably, the conductivity measuring device 28 will also detect alternating current from the sensor within a narrow band or range around the chosen excitation frequency and will include the digital processing capabilities needed to perform the conductivity calculation and compare the result to a pre-programmed maximum allowable conductivity level. The module will perform this calculation based upon a moving average algorithm that will prevent the activation or lighting of the warning light 30 in the event of a single, or a few spurious conductivity readings. In the event that the conductivities of fresh oil present in engine 20 are higher than the maximum allowable conductivity level for the used oil, the module will determine whether the oil conductivity is increasing or decreasing with time and will activate the oil change warning light 30 only if the oil conductivity is monotonically increasing from a previous minimum level. High conductivities in fresh oil may be caused by the presence of high levels of detergent or other desirable additives which may have high conductivities.

The electrodes 12 and 14 are preferably spaced apart by insulating spacers 32 and 34, as best shown in FIGS. 3 and 4. Rivets 33 and 35 or other suitable fasteners may be used to connect the insulating spacers 32 and 34 between the electrodes 12 and 14 in order to provide constant spacing of the concentric electrodes the desired distance (L) apart. In such as case, the rivets are held apart by the insulating spacers.

As previously mentioned, the outer electrode 12 is preferably grounded to the body of the plug 18 so that only a single wire is fed through plug 18 for connection to inner electrode 14. In an exemplary embodiment, the outer electrode 12 will have a diameter of 1.2 cm with the inner electrode 14 having a diameter of 0.8 cm. This provides an inter-electrode spacing (L) of 0.2 cm. In accordance with the previously described equations, the approximate cell constant for this cell using an average electrode diameter of 1.0 cm will be:

$$K = (L/A) = (0.2)/(3.14)(1.0) = 6 \times 10^{-2} \text{ cm}^{-1} \quad (5)$$

The cell constant (K) for the cell may also be determined by dipping the cell briefly in a standard potassium chloride solution and measuring the conductivity of the standard solution to establish the cell constant.

Assuming that the desired maximum allowable conductivity of oil is chosen to be about $1 \times 10^{-8}$ (Ohm/cm)$^{-1}$, the resistance of the oil may be calculated from equation 4 as:

$$R = K/k = (6 \times 10^{-2})/(1 \times 10^{-8}) = 6 \times 10^6 \text{ Ohms} \quad (6)$$

If 12 volts is applied across the electrodes 12 and 14, the current passing through the cell is:

$$i = V/R = (12)/(6 \times 10^6) = 2 \text{ micro/Amps} \quad (7)$$

An alternating current of 2 micro/Amps is relatively easy to measure, even in the electrically noisy environment of the automobile, and is a factor of 1000 times higher than the minimum current that can be measured by conventional conductivity equipment. Accordingly, the conductivity cell in accordance with the present invention provides a simple technique for measuring oil quality. If the maximum allowable conductivity of the oil is chosen to be higher than $1 \times 10^{-8}$ (Ohm/cm)$^{-1}$, the alternating current measurement will be even easier to make due to the increased microAmps flowing across the electrodes at a voltage of 12V. If desired, higher electrical current can be induced by increasing the voltage across the electrodes, increasing the surface area of electrodes or decreasing the inter-electrode spacing (L). A voltage of 12 volts is preferred since this is the standard voltage used in most automobiles and other vehicles utilizing internal combustion engines.

Although the present invention has been described with respect to mounting the concentric electrodes on a plug in the oil sump, it should be pointed out that the electrodes may be mounted anywhere within the internal combustion engine provided that the electrodes will remain immersed in engine oil during engine operation. Further, although concentric electrodes are preferred, other electrode shapes and configurations may be used provided that suitable AC conductivity measurements can be made.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A system for monitoring the accumulation of water and sulfuric acid contaminants in internal combustion engine oil, wherein said contaminants have an electrical conductivity which is different from the electrical conductivity of said oil, said system comprising:

an electrochemical cell comprising two electrodes which are spaced apart at a constant spacing to provide a conductivity measurement zone of constant width located between said electrodes, said electrochemical cell being capable of being immersed in said oil;

means for applying to said electrochemical cell an alternating current voltage having a frequency within the range of 100 to 1000 hertz; and means for measuring the alternating current conductivity of said oil in said conductivity measurement zone when said electrochemical cell is immersed in said oil to thereby indicate the amount of said water and sulfuric acid contaminants in said oil.

2. A system for monitoring the accumulation of contaminants in oil according to claim 1 which further includes warning means for indicating that the alternating current conductivity of said oil has reached a preselected maximum, said warning means being operable between an off mode when said alternating current conductivity is below said pre-selected maximum and an on mode when said alternating current conductivity is at or above said pre-selected maximum.

3. A system for monitoring the accumulation of contaminants in oil according to claim 1 wherein said electrodes comprise two concentric cylinders.

4. A system for monitoring the accumulation of contaminants in oil according to claim 3 wherein said oil is engine oil in an internal combustion engine and said electrodes are attached to a drain plug used for draining said oil from said internal combustion engine.

5. A system for monitoring the accumulation of contaminants in oil according to claim 3 wherein said concentric cylinders are made from metallic mesh.

6. A method for monitoring the accumulation of water and sulfuric acid contaminants in internal combustion engine oil wherein said contaminants have an electrical conductivity which is different from said oil and wherein said contaminants accumulate in said oil over a period of time to produce contaminated oil, said method comprising the steps of:

(a) providing two electrodes which are spaced apart at a constant spacing to provide a conductivity measurement zone of constant width located between said electrodes;

(b) immersing said two electrodes in said oil;

(c) applying an alternating current voltage to said two electrodes at a frequency within the range of 100–1000 hertz;

(d) measuring the alternating current voltage passing between said electrodes immersed in said oil during said period of time to thereby measure the alternating current conductivity of said oil in said conductivity measurement zone; and (e) monitoring the level of said alternating current conductivity to thereby indicate the amount of said water and sulfuric acid contaminants in said oil.

7. A method for monitoring the accumulation of contaminants in oil according to claim 6 wherein said contaminants are water and/or acid produced during operation of an internal combustion engine.

8. A method for monitoring the accumulation of contaminants according to claim 7 wherein measurement of the alternating current conductivity of said oil is accomplished by measuring the alternating current conductivity of the oil located between two concentric cylindrical electrodes.

9. A method for monitoring the accumulation of contaminants in oil according to claim 6 wherein measurement of the alternating current conductivity of said oil is accomplished by measuring the alternating current conductivity of said oil located between two concentric cylindrical electrodes.

10. A method for monitoring the accumulation of contaminants in the oil in an internal combustion engine according to claim 9 wherein said concentric cylindrical electrodes are attached to a drain plug used for draining said oil from said internal combustion engine.

* * * * *